United States Patent [19]
Sasaki et al.

[11] Patent Number: 5,879,702
[45] Date of Patent: Mar. 9, 1999

[54] ANALGESIC ANTI-INFLAMMATORY ADHESIVE PREPARATIONS

[75] Inventors: Yasuhiko Sasaki, Soka; Yukihiro Matsumura, Ootonemachi; Susumu Imai, Showamachi; Tetsuhiro Tooyama, Satte; Masamichi Orihara, Miyashiromachi; Yoshio Sugimoto, Kazo; Masaru Yamazaki, Showamachi; Mitsunari Hoshino; Yasumasa Uchikawa, both of Soka; Hiroshi Arai, Itakuramachi, all of Japan

[73] Assignee: Tokuhon Corporation, Tokyo, Japan

[21] Appl. No.: 3,504

[22] Filed: Jan. 6, 1998

Related U.S. Application Data

[62] Division of Ser. No. 547,336, Oct. 24, 1995, Pat. No. 5,776,484.

[30] Foreign Application Priority Data

Oct. 26, 1994 [JP] Japan ..................................... 6-284573

[51] Int. Cl.$^6$ ...................................................... A61K 9/70
[52] U.S. Cl. .................... 424/448; 424/449; 424/447; 424/486
[58] Field of Search .................... 424/447, 448, 424/449, 486

[56] References Cited

U.S. PATENT DOCUMENTS

| | | |
|---|---|---|
| 4,411,754 | 10/1983 | Kaetsu et al. . |
| 4,849,418 | 7/1989 | Lohner et al. . |
| 4,938,964 | 7/1990 | Sakai . |
| 4,996,209 | 2/1991 | Aoki . |
| 5,093,133 | 3/1992 | Wisniewski .............................. 424/484 |
| 5,206,029 | 4/1993 | Brune et al. ............................ 424/489 |
| 5,266,723 | 11/1993 | Hanna et al. ........................... 562/490 |
| 5,478,567 | 12/1995 | Nakagawa et al. ..................... 424/449 |
| 5,541,227 | 7/1996 | Loew et al. . |
| 5,702,720 | 12/1997 | Effing et al. ............................ 424/448 |

FOREIGN PATENT DOCUMENTS

| | | |
|---|---|---|
| 62-6536 | 12/1987 | Japan . |
| 64-40420 | 10/1989 | Japan . |
| 4-321624 | 11/1992 | Japan . |

*Primary Examiner*—James H. Reamer
*Attorney, Agent, or Firm*—Armstrong, Westerman, Hattori, McLeland & Naughton

[57] ABSTRACT

A non-steroidal analgesic anti-inflammatory adhesive preparation rendered by coating one surface of support with an adhesive containing S-(+)-2-(2-fluoro-4-biphenylyl) propionic acid and a styrene-isoprene-styrene block copolymer or S-(+)-2-(2-fluoro-4-biphenylyl) propionic acid and a modified copolymer in which methylmethacrylate is allowed to graft-polymerize on said copolymer, or with an adhesive containing S-(+)-2-(2-fluoro-4-biphenylyl) propionic acid, sodium carboxymethyl cellulose and sodium polyacrylate.

17 Claims, 2 Drawing Sheets

ANALGESIC ANTI-INFLAMMATORY ADHESIVE PREPARATIONS

The present application is a Divisional Application of U.S. application Ser. No. 08/547,336, filed Oct. 24, 1995 now U.S. Pat. No. 5,776,484.

BACKGROUND OF THE INVENTION

1. Field of the Invention

The present invention is related to a non-steroidal analgesic anti-inflammatory adhesive preparation which contains as the pharmacologically effective component S-(+)-2-(2-fluoro-4-biphenylyl) propionic acid [abbreviated S-(+)-FP hereinafter] which is optically resolved from the racemic modification 2-(2-fluoro-4-biphenylyl) propionic acid (also called: flurbiprofen).

2. Prior Art

Adhesive preparations, which can be broadly classified into poultices and plasters, are generally composed of a pharmacologically effective component, an adhesive which contains a plaster base as the principle components and further contains, as necessary, tackifiers, softeners, as well as solubilizing agents helpful in percutaneous absorption, and a flexible support which retains this adhesive in a layer shape. Then, a non-steroidal analgesic anti-inflammatory drug of one kind, or two or more kinds selected from methyl salicylate, glycol salicylate, emorfazone, diflunisal, oxaprozin, diclofenac, fenbufen, alclofenac, amfenac, indometacin, acemetacin, metiazinic acid, suprofen, ibuprofen, ketoprofen, flurbiprofen, fenoprofen, thiaprofen, tolmetin, naproxen, pranoprofen, protizinic acid, fentiazac, sulindac, clidanac, loxoprofen, lobenzarit, tolfenamic acid, flufenamic acid, and mefenamic acid, and their salts and esters etc. are normally used as the pharmacologically effective component of the non-steroidal analgesic anti-inflammatory adhesive preparation.

Not limited to non-steroidal analgesic anti-inflammatory adhesive preparations, the most important factor in all kinds of adhesive preparations is to be able to administer the pharmacologically effective component of adhesive preparation to the affected area percutaneously with good efficiency, and in order to realize this, several proposals were made in conventional technology.

For example, Japanese Patent Kokai No. 40,420/89 has the purpose of increasing the solubility of the non-steroidal analgesic anti-inflammatory drug into the plaster base, and also of increasing the percutaneous absorption. This patent indicated the use of styrene-isoprene-styrene block copolymers as the plaster base, polyterpene resin, terpene phenol resin or petroleum resin as the tackifier, liquid paraffin as the softener, and mentha oil as the solubilizing agent. Also, it is indicated in Japanese Patent Kokai No. 321,624/92 that, in order to improve the solubility of 4-biphenylacetic acid (also called: felbinac) which is one kind of analgesic anti-inflammatory drug, and of the ethyl esters thereof (also called: felbinac ethyl) into the plaster base, a styrene-isoprene-styrene block copolymer was selected for the plaster base, and this was used together with crotamiton.

In this regard, within all the kinds of non-steroidal analgesic anti-inflammatory drugs described above, flurbiprofen is synthesized as a racemic modification which a mixture of equal amount of dextrorotatory flurbiprofen and levorotatory flurbiprofen, and conventionally it was extremely difficult to resolve these racemic modifications. For this reason, if flurbiprofen is used as the non-steroidal analgesic anti-inflammatory drug, the precedent was to use these racemic modifications as is.

However, racemic flurbiprofen can be resolved into dextrorotatory flurbiprofen and levorotatory flurbidrofen by a method described in Patent Publication No. 6,536/87 entitled "Production Method for Optically Active 2-Aryl Propionic Acid."

One of the purposes of the present invention is to take advantage of the fact that dextrorotatory flurbiprofen has exceptionally superior efficacy as an analgesic anti-inflammatory drug for adhesive preparations than does racemic flurbiprofen, and offers a non-steroidal analgesic anti-inflammatory adhesive preparation which uses dextrorotatory flurbiprofen, namely, S-(+)-FP, as the pharmacologically effective component.

The other purpose of the present invention is to offer a plaster base which is suitable to the dissolution and dispersion of dextrorotatory flurbiprofen, a tackifier for this, as well as an assistant to promote the percutaneous absorption of dextrorotatory flurbiprofen.

SUMMARY OF THE INVENTION

Figure 1:
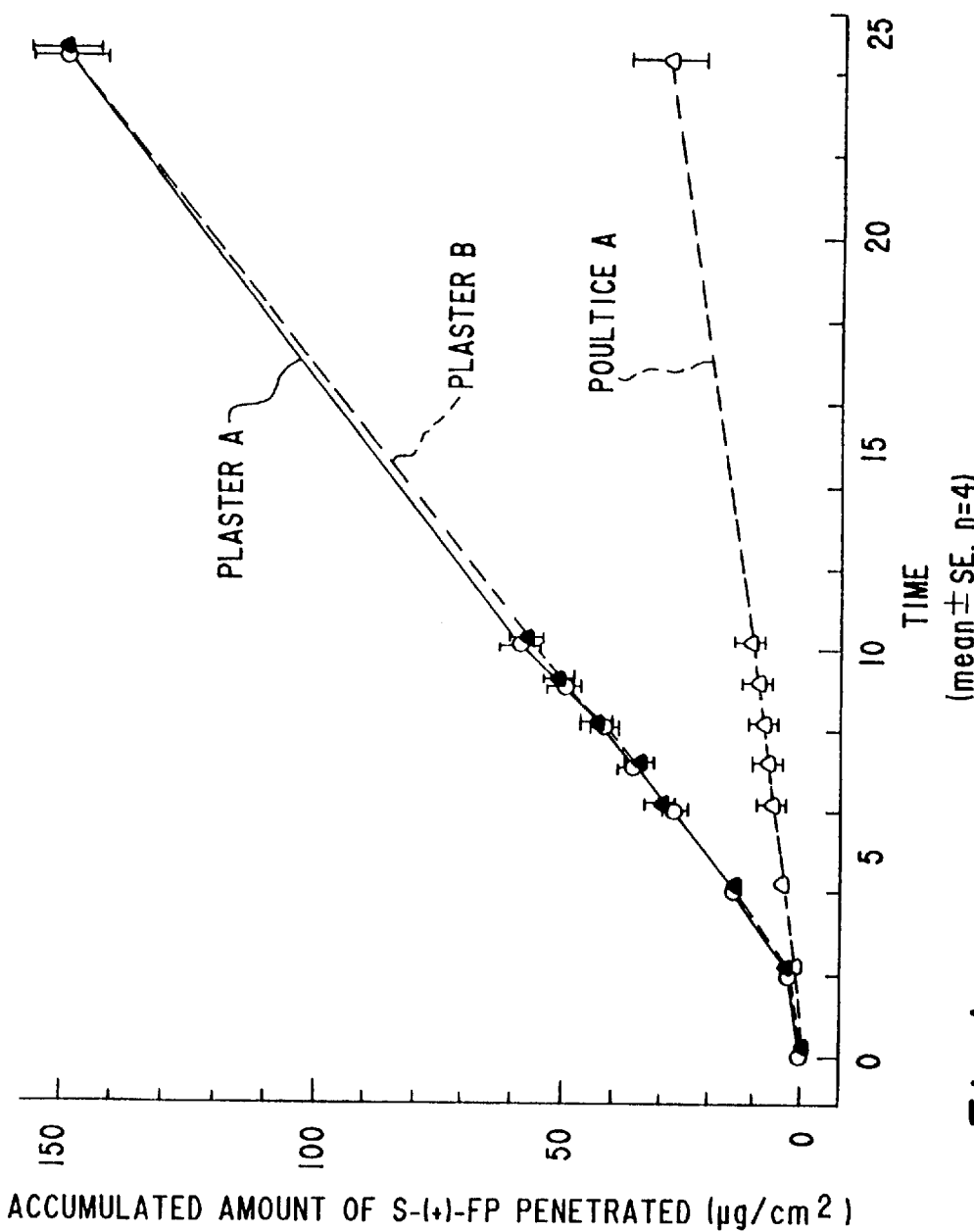
FIG. 1 is a graph indicating the skin penetration (in vitro) of pharmacologically effective component S-(+)-FP.

An object of the present invention is to provide a non-steroidal analgesic anti-inflammatory adhesive preparation rendered by coating one surface of support with an adhesive which contains a non-steroidal analgesic anti-inflammatory drug and a plaster base, characterized in that the said analgesic anti-inflammatory drug is S-(+)-2-(2-fluoro-4-biphenylyl)propionic acid, and the said plaster base is a styrene-isoprene-styrene block copolymer or a modified copolymer in which methylmethacrylate is allowed to graft-polymerize on said copolymer.

Said adhesive may further contains a rosin ester resin as a tackifier and/or mentha oil and at least one kind selected from the group comprising intermediate chain fatty acid asters of polyhydric alcohol as a promoter for percutaneous absorption of a pharmacologically effective component.

Another object of the present invention is to provide a non-steroidal analgesic anti-inflammatory adhesive preparation rendered by coating one surface of support with an adhesive which contains a non-steroidal analgesic anti-inflammatory drug and a plaster base, characterized in that the said analgesic anti-inflammatory drug is S-(+)-2-(2-fluoro-4-biphenylyl)propionic acid, and the said plaster base comprising sodium carboxymethyl cellulose and sodium polyacrylate.

Said adhesive may further contain an emulsion of polyacrylate esters and/or mentha oil and at least one kind selected from a group consisting of intermediate chain fatty acid esters of polyhydric alcohol.

DETAILED DESCRIPTION AND THE PREFERRED EMBODIMENTS OF THE INVENTION

In the present invention, S-(+)-FP, which is used as the pharmacologically effective component, can be obtained from racemic flurbiprofen by the method described in the previously introduced Patent Publication No. 6,536/87.

Specifically, a mixture of an inactive organic fluid diluent, for example, a petroleum distillate, and an optically active α-mono substituted alkylamine enantiomer salt of 2-(2- fluoro-4-biphenylyl) propionic acid is heated to at least 80° C. In this case, the aforementioned amine and diluent are selected such that the salt of the racemic acid and the amine indicates a solubllity 0.1–10% W/V in the diluent at the operating temperature. By having a part of the salt remain undissolved in the diluent, a part of the optical isomer of one of the acid components in the salt is converted to its enantiomer, and after that enantiomer increased and the salt of the acid component which increased compared to the other has been collected, S-(+)-FP can be obtained by making the salt acidic with dilute hydrochloric acid or dilute sulfuric acid and then extracting with ether.

In addition, the present invention substitutes dextrorotatory S-(+)-FP for racemic flurbiprofen as the pharmacologically effective component, and in this point therefore, it can be distinguished from conventional adhesive preparations which use racemic flurbiprofen, and, except for the racemic flurbiprofen, it is possible to combine the conventionally known non-steroid analgesic anti-inflammatory drugs to the adhesive preparation of the present invention.

Plasters, in which the adhesive that is coated on the flexible support is composed of an oily composition, and poultices, which entail aqueous compositions, are both included in the adhesive preparations of the present invention.

First, when explaining plasters of the present invention, any kind of support can be used if it is a flexible sheet-shaped support through which the pharmacologically effective component S-(+)-FP cannot substantially pass. To give specific examples of sheet-shaped support which can be used in the present invention, in addition to woven fabric and non-woven fabric, etc., the following can be cited: plastic films such as polyolefin film (polyethylene film in particular), polyester film, polyvinyl alcohol film, vinyl chloride film, urethane alloy and urethane-vinyl chloride copolymer film, ethylene-vinyl acetate film, polyvinylidene chloride unstretched multi-layer film; foam films comprising a blend of acryl or polystyrenepolybutadiene and polyisoprene; films in which metal was deposited on the aforementioned films, or further, sheets which laminated two or more kinds of these films.

Normally, the thickness of the support is approximately 500 μm or less, and preferably, a range of 30–500 μm is suitable.

The adhesive which is coated on the support has pharmacologically effective component S-(+)-FF and the plaster base as the essential components, and is prepared by compounding into this tackifiers, softeners, dissolution and absorption promotion assistants, etc. as necessary. The amount of pharmacologically effective component compounded in the adhesive of plasters of the present invention is prepared such that, in the state wherein the adhesive has been coated on the support, the aforementioned pharmacologically effective component is normally present on the support in a present density of 50–1000 μm/cm², with 70–500 μm/cm² being preferable.

Styrene-isoprene-styrene block copolymer (abbreviated SIS hereinafter) or a modified copolymer in which methylmethacrylate is graft polymerized with this copolymer (abbreviated SIS-MMA hereinafter) is utilized as the plaster base in the plaster of the present invention. SIS is commercially obtainable under the product name Cariflex TR1107 or TR1112 (manufactured by Shell Japan Limited). Also, SIS-MMA can be obtained by graft polymerizing methylmethacrylate with SIS using radiation induced polymerization, and the content of the methylmethacrylate included in this modified copolymer may be in the range of 5–10 wt %. SIS and SIS-MMA may be jointly used or used individually, and the amount compounded in the total adhesive is normally in the range of 10–50 wt %, with 20–40 wt % being preferable. Then, if both are used jointly, the weight ratio of SIS/SIS-MMA can be selected in the range of 1:5–5:1.

There is nothing to prevent the use of a plaster base other than SIS and SIS-MMA as the plaster base of a plaster in the present invention as long as the pharmacological effect of S-(+)-FP and its percutaneous absorption is not hindered. Synthetic rubbers such as butyl rubber, polyisobutylene, styrene-butadiene rubber and acrylic resins may be used as this kind of plaster base. An alkyl (meth)acrylate copolymer obtained from aliphatic alcohol with a carbon number of 4–18 and (meth)acrylic acid as well as a copolymer of the aforementioned alkyl (meth)acrylate and another functional monomer are preferable as this acrylic resin.

In addition, to give specific examples of the alkyl (meth)acrylate described above, the following may be cited: butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, methyl methacrylate, ethyl methacrylate, butyl methacrylate, isobutyl methacrylate, 2-ethylhexyl methacrylate, isooctyl methacylate, decyl methacrylate, isodecyl methacrylate, lauryl methacrylate, and stearyl methacrylate, etc.

Deproteinized natural rubber is also one plaster base that can be used jointly with SIS or SIS-MMA. Deproteinized natural rubber means a substance in which natural rubber is processed by protease, and protein, which is normally included in natural rubber at about 5% and which is a source substance for immediate allergies, is eliminated. The pharmacologically effective component S-(+)-FP which is used in the present invention has strong protein bonding, and even if deproteinized natural rubber is jointly used with SIS or SIS-MMA, the percutaneous absorption of the pharmacologically effective component will not be hindered.

If other plaster bases such as the synthetic rubbers, acrylic resins and deproteinized natural rubber described above, are used in the plaster base of the present invention, the amount used may be a total of 20 wt % or less of the whole plaster base.

Rosin ester resin, polyterpene resin, terpene phenol resin, coumarone-indene resin, and petroleum resins may be used as the tackifier of the plaster in the present invention, and among these, rosin ester resin is preferable, in particular, a hydrogenated rosin ester resin that has been produced by eliminating low boiling point fractions (specific example: Estergam HG manufactured by Arakawa Chemical Industries, Ltd.).

Additionally, YS-Resin manufactured by Yasuhara Chemical Co., Ltd. and Piccolyte manufactured by Hercules Japan, Ltd. may be used as polyterpene resin, YS-Polystar manufactured by Yasuhara Chemical Co., Ltd. may be used as the terpene phenol resin, and Quinton manufactured by Nippon Zeon Co., Ltd., Arkon manufactured by Arakawa Chemical Industries, Ltd. and Escorez manufactured by Exxon Chemical Japan Limited may be used as the petroleum resin.

The amount of tackifier compounded may be selected in the range of 10–60 wt % in the adhesive total standard, with 20–50 wt % being preferable.

It is preferable that an assistant to promote the percutaneous absorption of pharmacologically effective component S-(+)-FP, namely, a percutaneous absorption promoter, be compounded in the plaster of the present invention. Mentha oil or intermediate chain fatty acid eater of polyhydric alcohol (specific example: Sefsol manufactured by Nikko Chemicals Co., Ltd.) may be used as this percutaneous absorption promoter. These may be used individually or mixed together, and when used mixed together, the weight ratio of the intermediate chain fatty acid esters of polyhydric alcohol in relation to the mentha oil is preferably in the range of 1:5–5:1. The amount of percutaneous absorption promoter compounded is within the range of 0.5–20 wt % in the adhesive total standard, with 1–10 wt % being preferable.

In addition to being able to further compound such softeners as, for example, liquid paraffin into plasters of the present invention, well known anti-aging agents and fillers (inorganic compounds) may also be optionally compounded.

Next, in regard to poultices relating to the present invention, the supports for the plasters described above can also be used with the poultices.

In the same way as conventional poultices, poultices of the present invention are prepared by coating the support with adhesive which has the essential components of purified water, which is the moisture adjustment solubilizer, the pharmacologically effective component and the plaster base. Compounded into these essential components are moisturizers, inorganic fillers, consistency adjusters and cross linking agents, etc. as necessary. S-(+)-FP is used as the pharmacologically effective component in the poultice of the present invention, and the amount of said pharmacologically effective component compounded in the adhesive is prepared such that, in the state wherein the adhesive is coated on the support, the aforementioned pharmacologically effective component is normally present on the support in a present density of 5–1000 $\mu m/cm^2$, and with 70–1000 $\mu m/cm^2$ being preferable.

Moreover, in the present invention, sodium carboxymethyl cellulose (CMC) and sodium polyacrylate may be jointly used as the plaster base. The amount of CMC compounded may be selected in the range of 1–6 wt %, with 2–4 wt % being preferable, and the amount of sodium polyacrylate compounded may be selected in the range of 1–15 wt %, with 3–10 wt % being preferable.

Preferably, such alkyl polyacrylate esters as Nikasol TS-620 manufactured by Nippon Carbide Industries Co., Inc. and Primal N-580NF manufactured by Japan Acrylic Chemical Co., Ltd. are compounded as the tackifier in the adhesive of a poultice of the present invention, and the amount compounded may be in the range of 1–20 wt %, with 3–12 wt % being preferable.

Also, it is preferable that assistants to promote the percutaneous absorption of the pharmacologically effective component S-(+)-FP, namely, percutaneous absorption promoters, be compounded in the poultices of the present invention. Mentha oil or intermediate chain fatty acid esters of polyhydric alcohol (specific example: Sefsol manufactured by Nikko Chemicals Co., Ltd.) may be used as this percutaneous absorption promoter. These two may be used individually or mixed together, and when used mixed together, the weight ratio of the intermediate chain fatty acid esters of polyhydric alcohol in relation to the mentha oil is preferably in the range of 1:5–5:1. The amount of percutaneous absorption promoter compounded may be in the range of 0.1–4 wt %, with 0.3–2.0 wt % being preferable.

Other substances may optionally be further compounded in the plasters of the present invention, for example, inorganic fillers such as kaolin, and moisturizers such as glycerin.

The following effects can be obtained by the adhesive preparations of the present invention related to the selection of S-(+)-FP as the pharmacologically effect component, and to the use of substances which are particularly suitable to said pharmacologically effective component as the plaster base.
(1) Because the pharmacologically effective component is efficiently and continuously released from the adhesive and absorbed through the skin, a superior pharmacological effect can be continuously obtained.
(2) The adhesive preparation has potent self-adhesive strength, and is also extremely safe.
(3) The pharmacologically effective component is present in the adhesive in a stable manner.

In addition to these, by compounding rosin ester resins (if a plaster) and alkyl polyacrylate esters (if a poultice) in the adhesive as tackifiers, and by compounding mentha oil or intermediate chain fatty acid esters of polyhydric alcohol as the percutaneous absorption promoters, the adhesive strength of the adhesive preparation to the skin, the release characteristics of the pharmacologically effective component, as well as the percutaneous absorption can be improved significantly.

EXAMPLE

The plaster base and the softeners indicated in Table 1 were kneaded in a heated, pressurized type kneader, and the tackifier was added to this and further kneaded. Next, a solution in which S-(+)-FP had been dissolved in a mixed solution of mentha oil and Sefsol was added to the aforementioned kneaded substance, kneaded until uniform, and this kneaded substance was coated on the support to form adhesive layer. Immediately thereafter the adhesive layer was covered with releasing paper, and a plaster of the present invention was obtained by cutting this to the desired size.

Moreover, a poultice of the present invention was obtained by coating the adhesive precursors of the composition indicated in Table 2 onto the support.

In addition, both of the adhesive preparations indicated in Table 1 and Table 2 was prepared such that the same amount of S-(+)-FP (20 mg/7×10 $cm^2$) was contained in the same surface area.

TABLE 1

|  | Plaster A | Plaster B |
|---|---|---|
| Plaster Base |  |  |
| SIS | 35 wt % | 20 wt % |
| SIS-MMA | — | 20 wt % |
| Butyl rubber | — | 15 wt % |
| Polyisobutylene | 15 wt % | — |
| Tackifier |  |  |
| Estergum HG (manufactured by Arakawa Chemical Industries, Ltd.) | 35 wt % | 30 wt % |
| Softener |  |  |
| Liquid paraffin | 7 wt % | 7 wt % |
| Percutaneous Absorption Promoter |  |  |
| Mentha oil | 3 wt % | 4 wt % |
| Sefsol (manufactured by Nikko Chemicals Co., Ltd.) | 3 wt % | 2 wt % |
| Pharmacologically Effective Component |  |  |

TABLE 1-continued

|  | Plaster A | Plaster B |
|---|---|---|
| S-(+)-FP | 2 wt % | 2 wt % |

TABLE 2

|  | Poultice A |
|---|---|
| Plaster Base | |
| CMC | 4 wt % |
| Sodium polyacrylate | 5 wt % |
| Moisturizer | |
| glycerin | 25 wt % |
| Inorganic Filler | |
| Kaolin | 10 wt % |
| Tackifier | |
| Nikasol TS-620 | 6 wt % |
| (manufactured by Nippon Carbide | |
| Industries Co., Inc.) | |
| Percutaneous Absorption Promoter | |
| Mentha oil | 0.3 wt % |
| Sefsol | 0.3 wt % |
| (manufactured by Nikko Chemicals Co., Ltd.) | |
| Pharmacologically Effective Component | |
| S-(+)-FP | 0.2 wt % |
| Purified Water | 49.2 wt % |

Drug Effect Test 1 (In Vitro Test)

The abdominal hair of hairless rats (body weight 170 g) was removed with hair clippers under pentobarbital anesthesia, and the abdominal skin was resected. The resected skins were set on vertical type cells (effective penetration surface area: 2.83 cm$^2$; cell volume: 16 ml), and test adhesive preparations with a diameter of 1.9 cm were affixed on this skin. Next, while maintaining the temperature of these cells at 37° C., the receiver fluid within the cells was agitated with magnetic stirrer, and 0.5 ml of receiver liquid was sampled at fixed intervals, and the concentration of S-(+)-FP in the fluid was measured.

The results are indicated in FIG. 1. The mean within the diagram indicates the average value; SE indicates the standard error; and n indicates the number tested.

Drug Effect Test 2 (In Vivo Test)

After anesthetizing hairless rats (body weight 190 g) by administering 1.0 ml of 25% urethane aqueous solution into the abdominal cavity, the abdominal hair was removed with hair clippers, and the rats were secured in a securing device. The temperature was maintained at approximately 38° C. by placing on a heated electric blanket. Next, 35 cm$^2$/kg per body weight test adhesive preparations were attached to the abdominal area with the hair removed, and secured with surgical tape (Sumitomo 3M, Ltd.) which has replaced the central 3×5 cm portion with qualitative filter paper. The time period for applying the adhesive preparation was 30 hours. Up to 3 hours after peeling off the adhesive preparation, 0.3 ml of blood was sampled from the carotid artery of the rats, and after separating the plasma, the concentration of S-(+)-FP in the plasma was measured.

Figure 2:
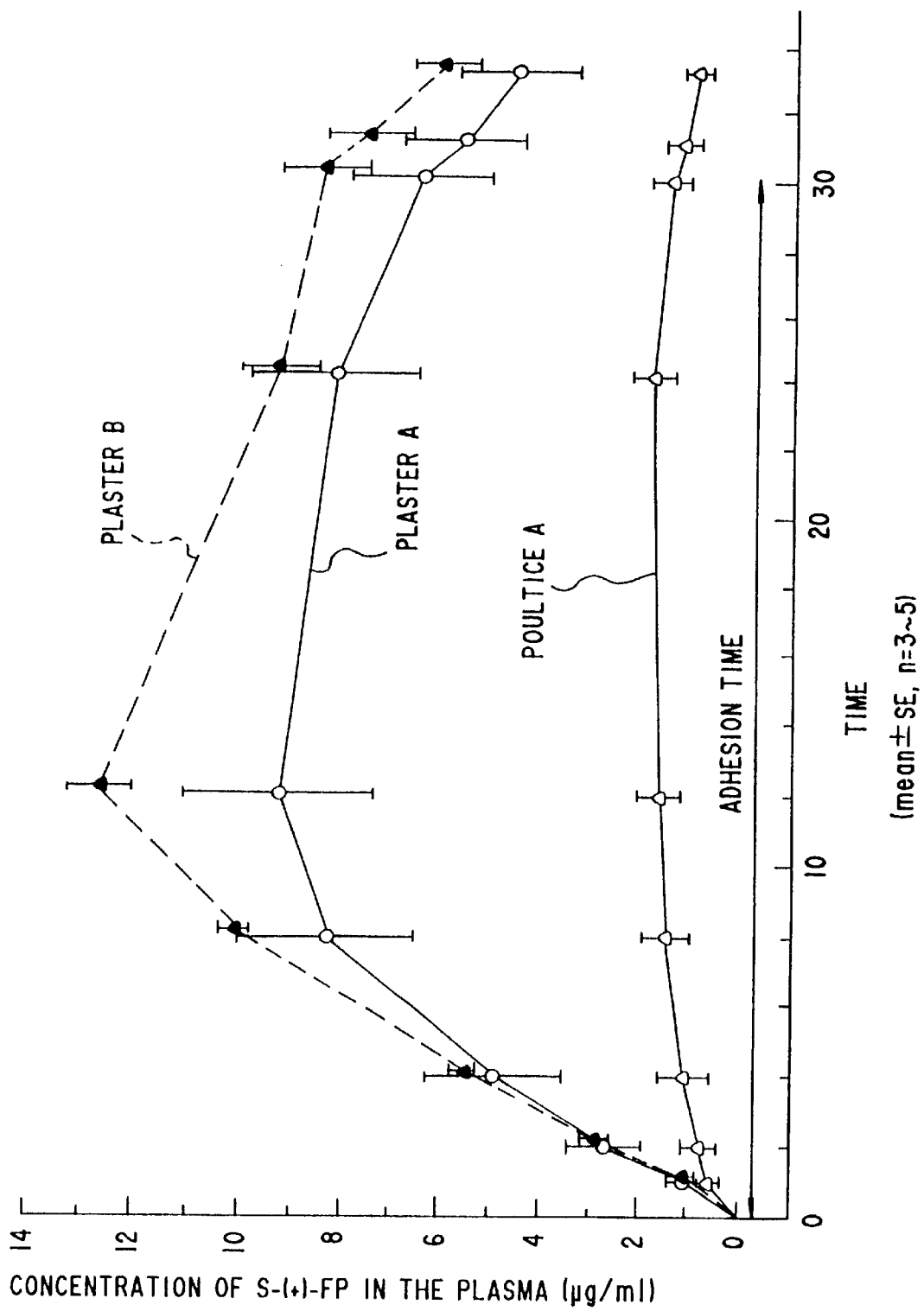
FIG. 2 is a graph indicating the concentration change of S-(+)-FP in the plasma.

The results are indicated in FIG. 2.

Drug Effect Test 3

Groups of eight Wistar strain rats (body weight approximately 145 g) were taken, and after measuring the volume of the right hind limb of each rat, the test adhesive preparation (3.0×3.5 cm) was affixed to the foot pad of the right hind limb. The adhesive preparation was peeled off after six hours, 0.1 ml of 1.0% lambda carrageenin physiological saline solution was immediately administered subcutaneously under the skin of that foot pad, and the volume of the foot was measured after 3 hours.

The edema rate was derived from the foot volume prior to the test and the foot volume after the test, and also, the suppression rate was derived from the difference with the control group (untreated). The results are indicated in Table 3.

TABLE 3

|  | Time Elapsed After Injection of Carrageenin | | | |
|---|---|---|---|---|
| Test | 3 hours | | 4 hours | |
| Adhesive Preparation | Edema rate (%) | Suppression rate (%) | Edema rate (%) | Suppression rate (%) |
| Control | 62.3 ± 1.7 | — | 65.6 ± 2.3 | — |
| Plaster A | 30.6 ± 3.1** | 50.8 | 39.4 ± 3.4 | 40.0 |
| Poultice A | 50.2 ± 2.2* | 19.4 | 58.8 ± 2.6 | 10.3 |

*p > 0.05
**p < 0.01 vs control

Drug Effect Test 4

Groups of ten Wistar strain rats (body weight approximately 110–30 g) were taken, the hair of the right hind limb of each rat was removed by an electric shaver under anesthesia the day before the test, and inflammation was induced by injecting 0.1 ml of 1% silver nitrate aqueous solution into the right knee cavitas articulare 18 hours prior to the test. On the day of the test, this right knee joint was bent five times; individuals which cried all five times were divided into groups such that the average body weight was nearly equal; and the test adhesive preparations were affixed for three hours to the inflamed knee joints. After peeling off the adhesive preparation, the presence or absence of cries induced by bending the inflamed leg joint five times was assessed every hour from 4.5 hours to 7.5 hours, and the pain suppression effect was measured by taking the frequency of cries as the score value. The results are indicated in Table 4.

TABLE 4

|  | Measurement Time | | | |
|---|---|---|---|---|
|  | 4.5 hr | 5.5 hr | 6.5 hr | 7.5 hr |
| Assessment Value: 0 | | | | |
| Control | 0/10 | 0/10 | 1/10 | 0/10 |
| Plaster A | 6/10 | 3/10 | 1/10 | 4/10 |
| Poultice A | 2/10 | 1/10 | 1/10 | 2/10 |
| Assessment Value: 0–1 | | | | |
| Control | 0/10 | 0/10 | 1/10 | 0/10 |
| Plaster A | 7/10 | 5/10 | 3/10 | 4/10 |
| Poultice A | 4/10 | 3/10 | 3/10 | 2/10 |
| Assessment Value: 0–2 | | | | |
| Control | 0/10 | 1/10 | 1/10 | 0/10 |
| Plaster A | 7/10 | 6/10 | 4/10 | 5/10 |

TABLE 4-continued

| | Measurement Time | | | |
|---|---|---|---|---|
| | 4.5 hr | 5.5 hr | 6.5 hr | 7.5 hr |
| Poultice A Assessment Value: 5 | 4/10 | 3/10 | 3/10 | 2/10 |
| Control | 9/10 | 8/10 | 10/10 | 9/10 |
| Plaster A | 2/10 | 2/10 | 3/10 | 4/10 |
| Poultice A | 1/10 | 5/10 | 5/10 | 7/10 |

Assessment Value: The frequency of cries when bending the inflamed joint five times.

What is claimed is:

1. A non-steroidal, analgesic anti-inflammatory adhesive plaster composition comprising:
   a) 1–6 wt % of a sodium carboxymethyl cellulose and 1–15 wt % of a sodium polyacrylate;
   b) 1–20 wt % of a tackifier; and
   c) 0.5–20 wt % of a percutaneous adsorption promoter;
   said adhesive composition containing 50–100 $\mu$m of (S)-(+)-2-(2-fluoro-4-biphenyl) propionic acid per $cm^2$ of the adhesive plaster composition.

2. A non-steroidal analgesic anti-inflammatory adhesive composition as claimed in claim 1, wherein said adhesive further contains an emulsion of polyacrylate esters.

3. A non-steroidal analgesic anti-inflammatory adhesive composition as claimed in claim 1, wherein said adhesive further contains a promoter for percutaneous absorption of a pharmacologically effective component of mentha oil and at least one kind selected from a group consisting of intermediate chain fatty acid esters of polyhydric alcohol.

4. A non-steroidal, analgesic anti-inflammatory adhesive plaster composition comprising:
   a) a plaster base; and
   b) (S)-(+)-2-(2-fluoro-4-biphenylyl) propionic acid.

5. The adhesive plaster composition of claim 4, further comprising a tackifier.

6. The adhesive plaster composition of claim 4, further comprising a percutaneous adsorption promoter.

7. The adhesive plaster composition of claim 4, further comprising a tackifier and a percutaneous adsorption promoter.

8. The adhesive composition of claim 4, wherein said plaster base comprises an alkyl(meth)acrylate copolymer.

9. The adhesive composition of claim 4, wherein said plaster base comprises an alkyl(meth)acrylate copolymer obtained from $C_4$–$C_{18}$ aliphatic alcohol and (meth)acrylic acid.

10. The adhesive composition of claim 8, wherein said alkyl(meth)acrylate is butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, methyl methacrylate, ethyl methacrylate, butyl methacrylate, isobutyl methacrylate, 2-ethylhexyl methacrylate, isooctyl methacrylate, decyl methacrylate, isodecyl methacrylate, lauryl methacrylate, and stearyl methacrylate.

11. The adhesive composition of claim 4, wherein said percutaneous absorption promoter is metha oil, an intermediate chain fatty acid ester of polyhydric alcohol or both.

12. The adhesive composition of claim 4, wherein said tackifier is an alkyl polyacrylate ester.

13. The adhesive composition of claim 1, wherein said percutaneous adsorption promoter is present in an amount of from 0.1 to 4 wt %.

14. A non-steroidal, analgesic anti-inflammatory adhesive plaster composition comprising:
   a) sodium carboxymethyl cellulose and sodium polyacrylate and
   b) (S)-(+)-2-(2-fluoro-4-biphenylyl) propionic acid.

15. The adhesive plaster composition of claim 14, further comprising a tackifier.

16. The adhesive plaster composition of claim 14, further comprising a percutaneous adsorption promoter.

17. The adhesive plaster composition of claim 14, further comprising a tackifier and a percutaneous adsorption promoter.

* * * * *